US008911749B2

(12) United States Patent
Ghartey-Tagoe et al.

(10) Patent No.: US 8,911,749 B2
(45) Date of Patent: Dec. 16, 2014

(54) VACCINE DELIVERY VIA MICRONEEDLE ARRAYS

(75) Inventors: Esi Ghartey-Tagoe, Sunnyvale, CA (US); Janet Wendorf, Redwood City, CA (US); Steve Williams, El Granada, CA (US); Parminder Singh, Union City, CA (US); Robert Wade Worsham, Cupertino, CA (US); Joseph C. Trautman, Sunnyvale, CA (US); Danir Bayramov, Irvine, CA (US); Danny Lee Bowers, Lake Odessa, MI (US); Andy Klemm, Ada, MI (US); Steven Richard Klemm, Grand Rapids, MI (US); Guohua Chen, Sunnyvale, CA (US)

(73) Assignee: Corium International, Inc., Menlo Park, CA (US)

(*) Notice: Subject to any disclaimer, the term of this patent is extended or adjusted under 35 U.S.C. 154(b) by 1149 days.

(21) Appl. No.: 12/249,795

(22) Filed: Oct. 10, 2008

(65) Prior Publication Data

US 2009/0155330 A1 Jun. 18, 2009

Related U.S. Application Data

(63) Continuation-in-part of application No. 12/148,180, filed on Apr. 16, 2008.

(60) Provisional application No. 60/998,498, filed on Oct. 10, 2007, provisional application No. 60/923,861, filed on Apr. 16, 2007, provisional application No. 60/925,262, filed on Apr. 18, 2007.

(51) Int. Cl.
*A61K 39/07* (2006.01)
*A61K 39/02* (2006.01)
*A61K 45/00* (2006.01)
*A61K 9/00* (2006.01)
*A61M 37/00* (2006.01)
*A61B 17/20* (2006.01)
*A61K 39/00* (2006.01)

(52) U.S. Cl.
CPC .............. *A61K 39/07* (2013.01); *A61K 9/0021* (2013.01); *A61K 2039/54* (2013.01); *A61M 37/0015* (2013.01); *A61B 17/205* (2013.01); *A61K 39/00* (2013.01)
USPC .................. 424/246.1; 424/234.1; 424/184.1; 424/278.1

(58) Field of Classification Search
None
See application file for complete search history.

(56) References Cited

U.S. PATENT DOCUMENTS

| 1,554,510 | A | 9/1925 | Kirby |
| 1,770,632 | A | 7/1930 | Smith |
| 2,046,240 | A | 6/1936 | Bayley |
| 2,434,407 | A | 1/1948 | George |
| 3,675,766 | A | 7/1972 | Rosenthal |
| 3,704,194 | A | 11/1972 | Harrier |
| 3,814,097 | A | 6/1974 | Ganderton et al. |
| 3,873,255 | A | 3/1975 | Kalwaites |
| 3,918,449 | A | 11/1975 | Pistor |
| 3,964,482 | A | 6/1976 | Gerstel et al. |
| 4,055,029 | A | 10/1977 | Kalbow |
| 4,117,841 | A | 10/1978 | Perrotta et al. |
| 4,151,240 | A | 4/1979 | Lucas et al. |
| 4,180,232 | A | 12/1979 | Hardigg |
| 4,342,314 | A | 8/1982 | Radel et al. |
| 4,381,963 | A | 5/1983 | Goldstein et al. |
| 4,395,215 | A | 7/1983 | Bishop |
| 4,402,696 | A | 9/1983 | Gulko |
| 4,460,368 | A | 7/1984 | Allison et al. |
| 4,460,370 | A | 7/1984 | Allison et al. |
| 4,463,045 | A | 7/1984 | Ahr et al. |
| 4,509,908 | A | 4/1985 | Mullane, Jr. |
| 4,515,168 | A | 5/1985 | Chester et al. |
| 4,556,441 | A | 12/1985 | Faasse, Jr. |
| 4,585,991 | A | 4/1986 | Reid et al. |
| 4,597,961 | A | 7/1986 | Etscom |
| 4,609,518 | A | 9/1986 | Curro et al. |
| 4,630,603 | A | 12/1986 | Greenway |
| 4,743,249 | A | 5/1988 | Loveland |
| 4,784,737 | A | 11/1988 | Ray et al. |
| 4,812,305 | A | 3/1989 | Vocal |
| 4,837,049 | A | 6/1989 | Byers et al. |

(Continued)

FOREIGN PATENT DOCUMENTS

| CA | 2376285 | 12/2000 |
| CA | 2316534 | 3/2001 |
| CA | 2422907 | 4/2002 |
| DE | 02319591 | 11/1974 |
| DE | 19518974 | 11/1995 |
| DE | 19624578 | 1/1998 |
| EP | 0156471 | 10/1985 |
| EP | 0240593 | 10/1987 |
| EP | 0301599 | 2/1989 |
| EP | 0312662 | 4/1989 |

(Continued)

OTHER PUBLICATIONS

International Search Report from PCT/US2001/031978 mailed on Apr. 29, 2002.

(Continued)

*Primary Examiner* — Rodney P Swartz
(74) *Attorney, Agent, or Firm* — Jacqueline F. Mahoney; Judy M. Mohr; McDermott Will & Emery LLP

(57) ABSTRACT

A microprojection array is provided, comprising an approximately planar base and a plurality of microprojections, wherein the array comprises a vaccine and a polymeric material. The array may have multiple layers. The vaccine may be placed in only one layer. In another embodiment of the invention, a method of preventing a disease is provided, comprising insertion into the skin of a patient an array of microprojections comprising a layer which comprises a vaccine for that disease and a polymer.

34 Claims, 1 Drawing Sheet

(56) References Cited

U.S. PATENT DOCUMENTS

| | | |
|---|---|---|
| 4,846,821 A | 7/1989 | Lyons et al. |
| 4,904,475 A | 2/1990 | Gale et al. |
| 4,966,159 A | 10/1990 | Maganias |
| 5,051,259 A | 9/1991 | Olsen et al. |
| 5,061,258 A | 10/1991 | Martz |
| 5,134,079 A | 7/1992 | Cusak et al. |
| 5,139,029 A | 8/1992 | Fishman et al. |
| 5,156,591 A | 10/1992 | Gross et al. |
| 5,158,073 A | 10/1992 | Bukowski |
| 5,160,315 A | 11/1992 | Heinecke et al. |
| 5,162,043 A | 11/1992 | Lew et al. |
| 5,190,558 A | 3/1993 | Ito |
| 5,198,192 A | 3/1993 | Saito et al. |
| 5,215,088 A | 6/1993 | Normann et al. |
| 5,244,677 A | 9/1993 | Kreckel et al. |
| 5,244,711 A | 9/1993 | Drelich et al. |
| 5,250,023 A | 10/1993 | Lee et al. |
| 5,250,067 A | 10/1993 | Gelfer et al. |
| 5,252,279 A | 10/1993 | Gore et al. |
| 5,256,360 A | 10/1993 | Li |
| 5,279,544 A | 1/1994 | Gross et al. |
| 5,308,625 A | 5/1994 | Wong et al. |
| 5,318,557 A | 6/1994 | Gross |
| 5,320,600 A | 6/1994 | Lambert |
| 5,330,452 A | 7/1994 | Zook |
| 5,362,307 A | 11/1994 | Guy et al. |
| 5,383,512 A | 1/1995 | Jarvis |
| 5,457,041 A | 10/1995 | Ginaven et al. |
| 5,462,743 A | 10/1995 | Turner et al. |
| 5,476,443 A | 12/1995 | Cartmell et al. |
| 5,487,726 A | 1/1996 | Rabinau et al. |
| 5,496,304 A | 3/1996 | Chasan |
| 5,498,235 A | 3/1996 | Flower |
| 5,503,843 A | 4/1996 | Santus et al. |
| 5,512,219 A | 4/1996 | Rowland et al. |
| 5,520,629 A | 5/1996 | Heinecke et al. |
| 5,527,288 A | 6/1996 | Gross et al. |
| 5,531,675 A | 7/1996 | Yoo |
| 5,531,855 A | 7/1996 | Heinecke et al. |
| 5,536,263 A | 7/1996 | Rolf et al. |
| 5,551,953 A | 9/1996 | Lattin et al. |
| 5,567,376 A | 10/1996 | Turi et al. |
| 5,591,123 A | 1/1997 | Sibalis et al. |
| 5,591,139 A | 1/1997 | Lin et al. |
| 5,611,806 A | 3/1997 | Jang |
| 5,645,977 A | 7/1997 | Wu et al. |
| 5,658,515 A | 8/1997 | Lee et al. |
| 5,662,127 A | 9/1997 | De Vaughn |
| 5,676,850 A | 10/1997 | Reed et al. |
| 5,681,580 A | 10/1997 | Jang et al. |
| 5,697,901 A | 12/1997 | Eriksson |
| 5,704,520 A | 1/1998 | Gross |
| 5,711,761 A | 1/1998 | Untereker et al. |
| 5,728,089 A | 3/1998 | Lal et al. |
| 5,730,714 A | 3/1998 | Guy et al. |
| 5,730,721 A | 3/1998 | Hyatt et al. |
| 5,735,273 A | 4/1998 | Kurnik et al. |
| 5,738,642 A | 4/1998 | Heinecke et al. |
| 5,756,117 A | 5/1998 | D'Angelo et al. |
| 5,771,890 A | 6/1998 | Tamada |
| 5,788,983 A | 8/1998 | Chien et al. |
| 5,800,420 A | 9/1998 | Gross et al. |
| 5,807,375 A | 9/1998 | Gross et al. |
| 5,814,020 A | 9/1998 | Gross |
| 5,820,622 A | 10/1998 | Gross et al. |
| 5,827,183 A | 10/1998 | Kurnik et al. |
| 5,843,114 A | 12/1998 | Jang |
| 5,848,985 A | 12/1998 | Muroki |
| 5,848,990 A | 12/1998 | Cirelli et al. |
| 5,848,991 A | 12/1998 | Gross et al. |
| 5,851,549 A | 12/1998 | Svec |
| 5,855,801 A | 1/1999 | Lin et al. |
| 5,873,849 A | 2/1999 | Bernard |
| 5,879,326 A | 3/1999 | Godshall et al. |
| 5,932,240 A | 8/1999 | D'Angelo et al. |
| 5,938,684 A | 8/1999 | Lynch et al. |
| 5,948,488 A | 9/1999 | Marecki et al. |
| 5,962,011 A | 10/1999 | DeVillez et al. |
| 5,964,729 A | 10/1999 | Choi et al. |
| 5,983,136 A | 11/1999 | Kamen |
| 5,987,989 A | 11/1999 | Yamamoto et al. |
| 5,997,549 A | 12/1999 | Sauceda et al. |
| 5,997,986 A | 12/1999 | Turi et al. |
| 6,014,584 A | 1/2000 | Hofmann et al. |
| 6,023,629 A | 2/2000 | Tamada |
| 6,024,553 A | 2/2000 | Shimalla |
| 6,036,659 A | 3/2000 | Ray et al. |
| 6,038,465 A | 3/2000 | Melton, Jr. |
| 6,038,485 A | 3/2000 | Axelgaard |
| 6,047,208 A | 4/2000 | Flower |
| 6,050,988 A | 4/2000 | Zuck |
| 6,055,453 A | 4/2000 | Hofmann et al. |
| 6,083,196 A | 7/2000 | Trautman et al. |
| 6,091,975 A | 7/2000 | Daddona et al. |
| 6,106,751 A | 8/2000 | Talbot et al. |
| 6,120,792 A | 9/2000 | Juni |
| 6,129,696 A | 10/2000 | Sibalis |
| 6,132,449 A | 10/2000 | Lum et al. |
| 6,132,755 A | 10/2000 | Eicher et al. |
| 6,135,990 A | 10/2000 | Heller et al. |
| 6,136,008 A | 10/2000 | Becker et al. |
| 6,156,336 A | 12/2000 | Bracht |
| 6,169,224 B1 | 1/2001 | Heinecke et al. |
| 6,181,964 B1 | 1/2001 | Hofmann et al. |
| 6,183,434 B1 | 2/2001 | Eppstein |
| 6,183,770 B1 | 2/2001 | Muchin et al. |
| 6,187,210 B1 | 2/2001 | Lebouitz et al. |
| 6,216,034 B1 | 4/2001 | Hofmann et al. |
| 6,219,574 B1 | 4/2001 | Cormier et al. |
| 6,230,051 B1 | 5/2001 | Cormier et al. |
| 6,241,701 B1 | 6/2001 | Hofmann |
| 6,256,533 B1 | 7/2001 | Yuzhakov et al. |
| 6,312,612 B1 | 11/2001 | Sherman et al. |
| 6,322,808 B1 | 11/2001 | Trautman et al. |
| 6,334,856 B1 | 1/2002 | Allen et al. |
| 6,355,054 B1 | 3/2002 | Neuberger |
| 6,375,627 B1 | 4/2002 | Mauze et al. |
| 6,375,870 B1 | 4/2002 | Visovsky et al. |
| 6,375,978 B1 | 4/2002 | Kleiner et al. |
| 6,379,324 B1 | 4/2002 | Gartstein et al. |
| 6,440,096 B1 | 8/2002 | Lastovich et al. |
| 6,451,240 B1 | 9/2002 | Sherman et al. |
| 6,471,903 B2 | 10/2002 | Sherman et al. |
| 6,476,288 B1 | 11/2002 | Van Rijswijck et al. |
| 6,494,830 B1 | 12/2002 | Wessel |
| 6,503,231 B1 | 1/2003 | Prausnitz et al. |
| 6,508,947 B2 | 1/2003 | Gulvin et al. |
| 6,511,463 B1 | 1/2003 | Wood et al. |
| 6,516,223 B2 | 2/2003 | Hofmann |
| 6,532,386 B2 | 3/2003 | Sun et al. |
| 6,533,884 B1 | 3/2003 | Mallik |
| 6,537,242 B1 | 3/2003 | Palmer |
| 6,537,264 B1 | 3/2003 | Cormier et al. |
| 6,558,361 B1 | 5/2003 | Yeshurun |
| 6,562,014 B2 | 5/2003 | Lin et al. |
| 6,565,532 B1 | 5/2003 | Yuzhakov et al. |
| 6,585,742 B2 | 7/2003 | Stough |
| 6,589,202 B1 | 7/2003 | Powell |
| 6,591,124 B2 | 7/2003 | Sherman et al. |
| 6,591,133 B1 | 7/2003 | Joshi |
| 6,603,987 B2 | 8/2003 | Whiston |
| 6,610,463 B1 | 8/2003 | Ohkura et al. |
| 6,611,706 B2 | 8/2003 | Avrahami et al. |
| 6,611,707 B1 | 8/2003 | Prausnitz et al. |
| 6,623,457 B1 | 9/2003 | Rosenberg |
| 6,629,949 B1 | 10/2003 | Douglas |
| 6,652,478 B1 | 11/2003 | Gartstein et al. |
| 6,656,147 B1 | 12/2003 | Gertsek et al. |
| 6,663,820 B2 | 12/2003 | Arias et al. |
| 6,685,682 B1 | 2/2004 | Heinecke et al. |
| 6,689,103 B1 | 2/2004 | Palasis |
| 6,691,752 B2 | 2/2004 | DiSabatino |
| 6,743,211 B1 | 6/2004 | Prausnitz et al. |
| 6,767,341 B2 | 7/2004 | Cho |

(56) References Cited

U.S. PATENT DOCUMENTS

| | | |
|---|---|---|
| 6,770,480 B1 | 8/2004 | Canham |
| 6,778,853 B1 | 8/2004 | Heller et al. |
| 6,780,171 B2 | 8/2004 | Gabel et al. |
| 6,808,506 B2 | 10/2004 | Lastovich et al. |
| 6,821,281 B2 | 11/2004 | Sherman et al. |
| 6,835,184 B1 | 12/2004 | Sage et al. |
| 6,855,131 B2 | 2/2005 | Trautman et al. |
| 6,881,203 B2 | 4/2005 | Delmore et al. |
| 6,931,277 B1 | 8/2005 | Yuzhakov et al. |
| 6,945,952 B2 | 9/2005 | Kwon |
| 6,960,193 B2 | 11/2005 | Rosenberg |
| 6,980,855 B2 | 12/2005 | Cho et al. |
| 7,011,844 B2 | 3/2006 | Gale et al. |
| 7,062,317 B2 | 6/2006 | Avrahami et al. |
| 7,087,035 B2 | 8/2006 | Trautman et al. |
| 7,097,631 B2 | 8/2006 | Trautman et al. |
| 7,108,681 B2 | 9/2006 | Gartstein et al. |
| 7,115,108 B2 | 10/2006 | Wilkinson et al. |
| 7,131,960 B2 | 11/2006 | Trautman et al. |
| 7,131,987 B2 | 11/2006 | Sherman et al. |
| 7,166,086 B2 | 1/2007 | Haider et al. |
| 7,184,826 B2 | 2/2007 | Cormier et al. |
| 7,186,235 B2 | 3/2007 | Martin et al. |
| 7,226,439 B2 | 6/2007 | Prausnitz et al. |
| 7,332,339 B2 | 2/2008 | Canham |
| 7,412,284 B2 | 8/2008 | Hofmann |
| 7,416,541 B2 | 8/2008 | Yuzhakov et al. |
| 7,572,405 B2 | 8/2009 | Sherman et al. |
| 7,578,954 B2 | 8/2009 | Gartstein et al. |
| 7,578,985 B2 | 8/2009 | Gartstein et al. |
| 7,611,481 B2 | 11/2009 | Cleary et al. |
| 7,763,203 B2 | 7/2010 | Arias et al. |
| 2001/0023324 A1 | 9/2001 | Pronovost et al. |
| 2001/0023351 A1 | 9/2001 | Eilers et al. |
| 2002/0006355 A1 | 1/2002 | Whiston |
| 2002/0016562 A1 | 2/2002 | Cormier et al. |
| 2002/0020688 A1 | 2/2002 | Sherman et al. |
| 2002/0032415 A1 | 3/2002 | Trautman et al. |
| 2002/0042589 A1 | 4/2002 | Marsoner |
| 2002/0045859 A1 | 4/2002 | Gartstein et al. |
| 2002/0045907 A1 | 4/2002 | Sherman et al. |
| 2002/0082543 A1 | 6/2002 | Park et al. |
| 2002/0087182 A1 | 7/2002 | Trautman et al. |
| 2002/0091357 A1 | 7/2002 | Trautman et al. |
| 2002/0096488 A1 | 7/2002 | Gulvin et al. |
| 2002/0133129 A1 | 9/2002 | Arias et al. |
| 2002/0133137 A1 | 9/2002 | Hofmann |
| 2002/0138049 A1 | 9/2002 | Allen et al. |
| 2002/0169411 A1 | 11/2002 | Sherman et al. |
| 2002/0177839 A1 | 11/2002 | Cormier et al. |
| 2002/0177858 A1 | 11/2002 | Sherman et al. |
| 2002/0188245 A1 | 12/2002 | Martin et al. |
| 2002/0193729 A1 | 12/2002 | Cormier et al. |
| 2003/0093028 A1 | 5/2003 | Spiegel |
| 2003/0093089 A1 | 5/2003 | Greenberg |
| 2003/0135167 A1 | 7/2003 | Gonnelli |
| 2003/0166624 A1 | 9/2003 | Gale et al. |
| 2003/0187394 A1 | 10/2003 | Wilkinson et al. |
| 2003/0199810 A1 | 10/2003 | Trautman et al. |
| 2003/0199812 A1 | 10/2003 | Rosenberg |
| 2003/0208138 A1 | 11/2003 | Olson |
| 2003/0208167 A1 | 11/2003 | Prausnitz et al. |
| 2003/0212397 A1 | 11/2003 | Avrahami et al. |
| 2003/0220610 A1 | 11/2003 | Lastovich et al. |
| 2003/0220656 A1 | 11/2003 | Gartstein et al. |
| 2004/0087992 A1 | 5/2004 | Gartstein et al. |
| 2004/0096455 A1 | 5/2004 | Maa et al. |
| 2004/0143211 A1 | 7/2004 | Haider et al. |
| 2004/0146611 A1 | 7/2004 | Arias et al. |
| 2004/0164454 A1 | 8/2004 | Gartstein et al. |
| 2004/0181203 A1 | 9/2004 | Cormier et al. |
| 2004/0186419 A1 | 9/2004 | Cho et al. |
| 2004/0204669 A1 | 10/2004 | Hofmann |
| 2004/0220535 A1 | 11/2004 | Canham |
| 2004/0236271 A1 | 11/2004 | Theeuwes et al. |
| 2005/0049549 A1* | 3/2005 | Wong et al. ................... 604/46 |
| 2005/0089554 A1 | 4/2005 | Cormier et al. |
| 2005/0096586 A1 | 5/2005 | Trautman et al. |
| 2005/0163827 A1 | 7/2005 | Zech et al. |
| 2005/0197308 A1 | 9/2005 | Dalton et al. |
| 2005/0209565 A1 | 9/2005 | Yuzhakov et al. |
| 2005/0228340 A1 | 10/2005 | Cleary et al. |
| 2006/0024358 A1* | 2/2006 | Santini et al. ................ 424/448 |
| 2006/0076718 A1 | 4/2006 | Sherman et al. |
| 2006/0095061 A1 | 5/2006 | Trautman et al. |
| 2006/0129174 A1 | 6/2006 | Gartstein et al. |
| 2007/0027427 A1 | 2/2007 | Trautman et al. |
| 2008/0114298 A1 | 5/2008 | Cantor et al. |
| 2008/0183144 A1 | 7/2008 | Trautman et al. |
| 2008/0195035 A1 | 8/2008 | Frederickson et al. |
| 2008/0269685 A1 | 10/2008 | Singh et al. |
| 2009/0155330 A1 | 6/2009 | Ghartey-Tagoe et al. |
| 2010/0028390 A1 | 2/2010 | Cleary et al. |

FOREIGN PATENT DOCUMENTS

| | | |
|---|---|---|
| EP | 0400249 | 12/1990 |
| EP | 0407063 | 1/1991 |
| EP | 0796128 | 9/1997 |
| EP | 1086718 A1 | 3/2001 |
| EP | 1086719 | 3/2001 |
| EP | 1174078 | 1/2002 |
| FR | 2535602 | 5/1984 |
| GB | 0783479 | 9/1957 |
| GB | 2221394 | 2/1990 |
| GB | 2277202 | 10/1994 |
| JP | 46-037758 | 12/1971 |
| JP | 60-242042 | 12/1985 |
| JP | 62-213763 | 9/1987 |
| JP | 01-264839 | 10/1989 |
| JP | 02-009755 | 3/1990 |
| JP | 03-151951 | 6/1991 |
| JP | 05-123326 | 5/1993 |
| JP | 05-162076 | 6/1993 |
| JP | 06-238644 | 8/1994 |
| JP | 07-132119 | 5/1995 |
| JP | 08-502215 | 3/1996 |
| JP | 09-051878 | 2/1997 |
| JP | 54-028369 | 3/1997 |
| JP | 09-140687 | 6/1997 |
| JP | 09-211022 | 8/1997 |
| JP | 10-328168 | 12/1998 |
| JP | 11-230707 | 8/1999 |
| JP | 11-509123 | 8/1999 |
| JP | 2000-146777 | 5/2000 |
| JP | 2000-147229 | 5/2000 |
| JP | 2000-164890 | 6/2000 |
| JP | 2000-194142 | 7/2000 |
| JP | 2000-232095 | 8/2000 |
| JP | 2000-232971 | 8/2000 |
| JP | 2000-322780 | 11/2000 |
| JP | 2000-323461 | 11/2000 |
| JP | 2001-004442 | 1/2001 |
| JP | 2001-138300 | 5/2001 |
| JP | 2001-149485 A | 6/2001 |
| JP | 2001-157715 | 6/2001 |
| JP | 2001-341314 | 12/2001 |
| JP | 2002-079499 | 3/2002 |
| JP | 2002-151395 | 5/2002 |
| JP | 2002-239014 | 8/2002 |
| JP | 2002-301698 | 10/2002 |
| JP | 2003-039399 | 2/2003 |
| JP | 2003-048160 | 2/2003 |
| JP | 2003-048180 | 2/2003 |
| SU | 1641346 | 4/1991 |
| SU | 1667864 | 8/1991 |
| SU | 1667884 | 8/1991 |
| WO | WO 93/15701 | 8/1993 |
| WO | WO 93/17754 | 9/1993 |
| WO | WO 94/23777 | 10/1994 |
| WO | WO 95/22612 | 8/1995 |
| WO | WO 95/33612 | 12/1995 |
| WO | WO 96/00109 | 1/1996 |
| WO | WO 96/00109 | 4/1996 |

(56) References Cited

FOREIGN PATENT DOCUMENTS

| | | |
|---|---|---|
| WO | WO 96/17648 | 6/1996 |
| WO | WO 96/37155 | 11/1996 |
| WO | WO 96/37256 | 11/1996 |
| WO | WO 97/03718 | 2/1997 |
| WO | WO 97/13544 | 4/1997 |
| WO | WO 97/48440 | 12/1997 |
| WO | WO 97/48441 | 12/1997 |
| WO | WO 97/48442 | 12/1997 |
| WO | WO 98/00193 | 1/1998 |
| WO | WO 98/28307 | 7/1998 |
| WO | WO 99/00155 | 1/1999 |
| WO | WO 99/29298 | 6/1999 |
| WO | WO 99/29364 | 6/1999 |
| WO | WO 99/29365 | 6/1999 |
| WO | WO 99/61888 | 12/1999 |
| WO | WO 99/64580 | 12/1999 |
| WO | WO 00/05166 | 2/2000 |
| WO | WO 00/35530 | 6/2000 |
| WO | WO 00/70406 | 11/2000 |
| WO | WO 00/74763 | 12/2000 |
| WO | WO 00/74764 | 12/2000 |
| WO | WO 00/74765 | 12/2000 |
| WO | WO 00/74766 | 12/2000 |
| WO | WO 00/77571 | 12/2000 |
| WO | WO 01/08242 | 2/2001 |
| WO | WO 01/36037 | 5/2001 |
| WO | WO 01/36321 | 5/2001 |
| WO | WO 01/49362 | 7/2001 |
| WO | WO 02/02180 | 1/2002 |
| WO | WO 02/07543 | 1/2002 |
| WO | WO 02/07813 | 1/2002 |
| WO | WO 02/17985 | 3/2002 |
| WO | WO 02/32331 | 4/2002 |
| WO | WO 02/32480 | 4/2002 |
| WO | WO 02/062202 | 8/2002 |
| WO | WO 02/072189 | 9/2002 |
| WO | WO 02/091922 | 11/2002 |
| WO | WO 02/100474 | 12/2002 |
| WO | WO 03/024290 | 3/2003 |
| WO | WO 03/024518 | 3/2003 |
| WO | WO 2004/076339 | 9/2004 |
| WO | WO 2004/110717 | 12/2004 |
| WO | WO 2005/094526 | 10/2005 |
| WO | WO 2006/020842 | 2/2006 |
| WO | WO 2006/055795 | 5/2006 |
| WO | WO 2007/002523 | 1/2007 |
| WO | WO 2007/124411 | 11/2007 |
| WO | WO 2008/011625 | 1/2008 |
| WO | WO 2008/091602 | 7/2008 |
| WO | WO 2008/130587 | 10/2008 |
| WO | WO 2009/048607 A1 | 4/2009 |

OTHER PUBLICATIONS

International Search Report from PCT/US2002/014624 mailed on Sep. 3, 2002.
International Search Report from PCT/US2008/004943 mailed on Jun. 9, 2009.
International Search Report from PCT/US2008/011635 mailed on Dec. 19, 2008.
McAllister, et al., "Micromachined microneedles for transdermal drug delivery", Am. Inst. Chem. Eng., 1998 Annual Meeting, Miami Beach, FL, Nov. 15-20, Drug Delivery II. pp. 1-4.
Papautsky, et al., "Micromachined Pipette Arrays," MPA, Proceedings—19th international Conference—IEEE/EMBS, Chicago IL, USA pp. 2281-2284 (1997).
Park, et al. "Polymer Microneedies for Controlled-Release Drug Delivery," Pharmaceutical Research, Kluwer Academic Publishers—Pienum Publishers, NE, vol. 23, No. 5, pp. 1008-1019 (2006).
Prausnitz, "Transdermal delivery of macromolecules: Recent advances by modification of skin's barrier properties", ACS Symposium Series No. 675, Therapeutic Protein and Peptide Formulation and Delivery, American Chemical Society, Washiraton DC, Chapter 8, pp. 124-153, (1997).
Matriano et al., "Macroflux Microprojection Array Patch Technology: A New and Efficient Approach for Intracutaneous Immunization", Pharmaceutical Research, Jan. 2002, 63-70, 19:1.
Mikszta et al., "Protective Immunization against Inhalational Anthrax: A Comparison of Minimally Invasive Delivery Platforms", The Journal of Infectious Diseases, 2005, 191:278-288.
Mikszta et al., "Improved genetic immunization via micromechanical disruption of skin-barrier function and targeted epidermal delivery", Nature Medicine, 2002, 8:4, 415-419.
Sivamani et al., "Microneedles and transdermal applications", Expert Opinion Drug Delivery, 2007, 4:1, 19-25.
PCT Search Report dated Dec. 10, 2008.
Chun, et al., "An array of hollow microcapillaries for the controlled injection of genetic materials into animal/plant cells," IEEE Workshop on Micro Electro Mechanical Systems, pp. 406-411, (1999).
Henry, et al., "Micromachined microneedles for transdermal delivery of drugs", IEEE Workshop on Micro Electro Mechanical Systems, New York, NY, pp. 494-498, (1998).
Henry, et al., "Microfabricated microneedles: A novel approach to transdermal drug delivery", J. Pharmaceutical Science, vol. 87, No. 8, pp. 922-925, (1998).
"Heparin Pregnancy and Breast Feeding Warnings", Drugs.com, Accessed Oct. 8, 2009, <http://www.drugs.com/pregnancy/heparin.html>.
International Search Report from PCT/US2000/015612 mailed on Sep. 7, 2000.
International Search Report from PCT/US2000/015613 mailed on Sep. 6, 2000.
International Search Report from PCT/US2000/015614 mailed on Sep. 6, 2000.
International Search Report from PCT/US2001/031977 mailed on Apr. 29, 2002.
International Search Report from PCT/US2001/031978 mailed on Apr. 29, 2002.
International Search Report from PCT/US2002/014624 mailed on Sep. 3, 2002.
International Search Report from PCT/US2002/029228 mailed on Apr. 23, 2003.
International Search Report from PCT/US2002/029245 mailed on Dec. 27, 2002.
International Search Report from PCT/US2004/005382 mailed on Nov. 25, 2004.
International Search Report from PCT/US2004/017255 mailed on May 24, 2005.
International Search Report from PCT/US2005/009854 mailed on Jul. 3, 2008.
International Search Report from PCT/US2008/000824 mailed on Jul. 18, 2008.
McAllister, et al., "Micromachined microneedles for transdermal drug delivery", Am. Inst. Chem. Eng., 1998 Annual Meeting, Miami Beach, FL, Nov. 15-20, Drug Delivery II, pp. 1-4.
Papautsky, et al., "Micromachined Pipette Arrays," MPA, Proceedings—19th international Conference—IEEE/EMBS, Chicago IL, USA, pp. 2281-2284 (1997).
Park, et al. "Polymer Microneedles for Controlled-Release Drug Delivery," Pharmaceutical Research, Kluwer Academic Publishers—Plenum Publishers, NE, vol. 23, No. 5, pp. 1008-1019 (2006).
Prausnitz, et al., "Transdermal transport efficiency during skin electroporation and iontophoresis", J. Contr. Release, vol. 38, pp. 205-217, (1996).
Prausnitz, "Transdermal delivery of macromolecules: Recent advances by modification of skin's barrier properties", ACS Symposium Series No. 675, Therapeutic Protein and Peptide Formulation and Delivery, American Chemical Society, Washington DC, Chapter 8, pp. 124-153, (1997).
Rydberg, et al., "Low-molecular-weight heparin preventing and treating DVT", Am. Fam. Physician, vol. 59, No. 6, pp. 1607-1612, (1999).
Wouters, et al., "Microelectrochemical systems for drug delivery", Electrochimica Acta., vol. 42, pp. 3385-3390, (1997).
Xia, et al., "Soft Lithography", Angew. Chem. Int. Ed., vol. 37, pp. 551-575, (1998).
Xia, et al., "Soft Lithography", Annu. Rev. Mater. Sci., vol. 28, pp. 153-184 (1998).

* cited by examiner

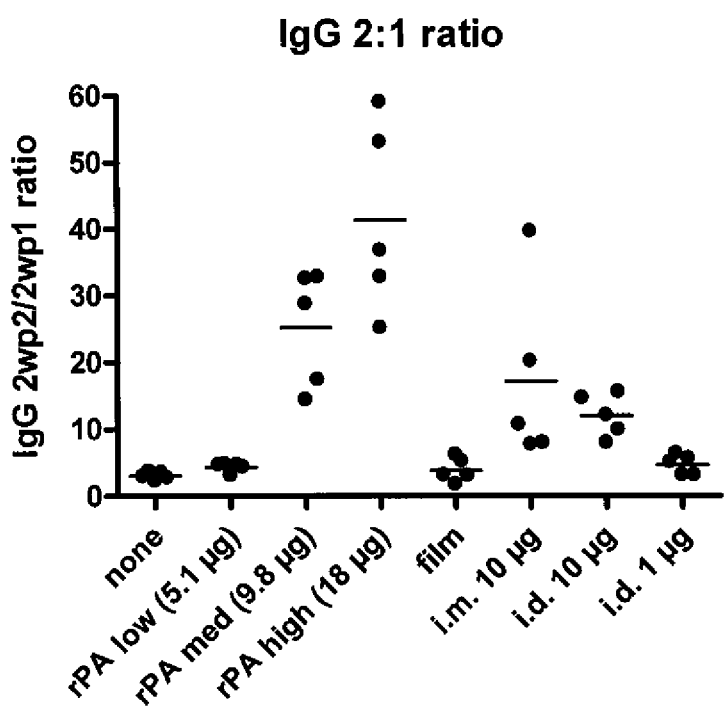

VACCINE DELIVERY VIA MICRONEEDLE ARRAYS

CROSS-REFERENCE TO RELATED APPLICATIONS

This application claims priority to U.S. Provisional Application Ser. No. 60/998,498, filed Oct. 10, 2007. This application also claims priority to U.S. patent application Ser. No. 12/148,180, filed Apr. 16, 2008, which claims priority to U.S. Provisional Application Ser. No. 60/923,861, filed Apr. 16, 2007, and U.S. Provisional Application Ser. No. 60/925,262, filed Apr. 18, 2007. These priority applications are incorporated by reference herein in their entirety.

TECHNICAL FIELD

This invention relates generally to drug delivery using microneedles or other microprotrusions or microprojections.

BACKGROUND

Protection against pathogenic bacteria and viruses (as well as other pathogenic microbes, including parasites and fungi) can be conferred on an individual in three ways: a) passive immunization—direct infusion of antibodies raised against a specific organism, b) prior exposure to the micro-organism itself, or c) prophylactic vaccination against the organism. In the two latter cases, the exposed individual's adaptive immune system is activated at both the humoral and cellular levels. Humoral responses involve production of antibodies against the pathogen (or a component of it) by circulating B lymphocytes; the antibodies bind to the organism, thus tagging it for destruction or removal by other elements of the immune system. Cellular responses are complex, and involve activation of many different cell types within the host's immune system (including the innate immune system components); these cells are then either directly or indirectly involved in the destruction or removal of the pathogen, or host cells that may already be infected by the pathogen. For general background on vaccination one may consult, for example, Charles A. Janeway et al., *Immunobiology* (6th ed. 2004).

A key step in the immunization process is to ensure that the antigen is delivered to a tissue that contains antigen presenting cells (APCs). These cells are responsible for acquiring immunogenic components of potential pathogens, and displaying them on their cell surface in such a way that they interact successfully with key components of the immune system to mount the robust humoral and/or cellular response required for protective immunity.

The density of APCs in muscle tissue is considerably lower than that in the epidermal layer of the skin. However, vaccines are normally administered via direct injection into muscle, a procedure that has been dictated more by convenience for the health care practitioner than by the role that muscle tissue plays in the immune system. The pain and bleeding that often results from damage to blood vessels (muscle being highly vascularized) can result in poor patient compliance.

The epidermal layer of the skin is a convenient tissue for antigen delivery since it contains neither nerves nor blood vessels and it is rich in a specialized type of APC, the Langerhans cell. Delivery of vaccine components to this tissue is often referred to as "transcutaneous" immunization. Transcutaneous immunization may be achieved by use of ordinary needles in an intradermal mode of delivery. It is commonly carried out using adjuvants. "Transcutaneous immunization (TCI) is a new method of vaccination that utilizes a topical application of an adjuvant and vaccine antigen to intact skin to induce an immune response." Gregory M. Glenn et al., "Transcutaneous immunization: a human vaccine delivery strategy using a patch," *Nature Medicine*, vol. 6, 1403-1406 (2000). See also U.S. Published Patent Application No. 2007/0088248.

Arrays of microneedles were proposed as a way of administering drugs through the skin in the 1970s, for example in expired U.S. Pat. No. 3,964,482. Microneedle arrays can facilitate the passage of drugs through or into human skin and other biological membranes in circumstances where ordinary transdermal or topical administration is inadequate. Microneedle arrays can also be used to sample fluids found in the vicinity of a biological membrane such as interstitial fluid, which is then tested for the presence of biomarkers.

Despite much initial work on fabricating microneedle arrays in silicon or metals, there are significant advantages to polymeric arrays. U.S. Pat. No. 6,451,240 discloses some methods of manufacturing polymeric microneedle arrays. Arrays made primarily of biodegradable polymers have some advantages. U.S. Pat. No. 6,945,952 and U.S. Published Patent Applications Nos. 2002/0082543 and 2005/0197308 have some discussion of microneedle arrays made of biodegradable polymers.

Microneedle arrays are believed to have advantages for vaccine delivery. See, for example, James A. Matriano et al., "Macroflux® Microprojection Array Patch Technology: A New and Efficient Approach for Intracutaneous Immunization," *Pharmaceutical Research*, vol. 19, p. 63 (2002).

There is therefore a need for an effective means of delivering vaccines via microneedles and of making use of the advantages of microneedle delivery for vaccines.

SUMMARY OF THE INVENTION

A microprojection array is provided, comprising an approximately planar base and a plurality of microprojections, wherein the array comprises a vaccine and a polymeric material. The array may have multiple layers. The vaccine may be placed in only one layer.

In another embodiment of the invention, a method of preventing a disease is provided, comprising insertion into the skin of a patient an array of microprojections comprising a layer which comprises a vaccine for that disease and a polymer.

FIGURES

FIG. 1 depicts the ratios of IgG titer two weeks after the priming dose (denoted 2wp1) and two weeks after the treatment being tested (denoted 2wp2), for each group of animals tested in Example 4.

DETAILED DESCRIPTION OF PREFERRED EMBODIMENTS

Before describing the present invention in detail, it is to be understood that this invention is not limited to specific solvents, materials, or device structures, as such may vary. It is also to be understood that the terminology used herein is for the purpose of describing particular embodiments only, and is not intended to be limiting.

As used in this specification and the appended claims, the singular forms "a," "an," and "the" include both singular and plural referents unless the context clearly dictates otherwise. Thus, for example, reference to "an active ingredient"

includes a plurality of active ingredients as well as a single active ingredient, reference to "a temperature" includes a plurality of temperatures as well as single temperature, and the like.

In this application reference is often made for convenience to "skin" as the biological membrane through which the active is administered. It will be understood by persons of skill in the art that in some instances the same inventive principles apply to administration through other biological membranes such as those which line the interior of the mouth, gastro-intestinal tract, blood-brain barrier, or other body tissues or organs or biological membranes which are exposed during surgery or during procedures such as laparoscopy or endoscopy.

The terms "microprojection" and "microprotrusion" are commonly employed in the literature to denote volumes of roughly sub-millimeter to roughly sub-micron size which project or protrude outward from a surface. In this application reference is also made to "microneedles" as the type of microprotrusion or microprojection which is being employed. It will be understood by persons of skill in the art that in many cases the same inventive principles apply to the use of other microprotrusions or microprojections to penetrate skin or other biological membranes. Other microprotrusions or microprojections may include, for example, microblades as described in U.S. Pat. No. 6,219,574 and Canadian patent application no. 2,226,718, and edged microneedles as described in U.S. Pat. No. 6,652,478.

A microprojection array is provided, comprising an approximately planar base and a plurality of microprojections, wherein the array comprises a vaccine and a polymeric material. The array may comprise multiple layers. The vaccine may be placed in only one layer.

In another embodiment of the invention, a method of preventing a disease is provided, comprising insertion into the skin of a patient an array of microprojections comprising a layer which comprises a vaccine for that disease and a polymer.

The microprojection arrays of the invention may be inserted into the skin and then removed after a period of time. The whole (or part) of the vaccine or polymer-containing microprojection array layer may be left behind in the skin. The insertion may be, for example, for no more than about 2 minutes, no more than about 5 minutes, no more than about 10 minutes, or no more than about 30 minutes.

A. Vaccines

The microprojection arrays of the invention are advantageously used for the delivery of a variety of vaccines. These vaccines may include, for example, those approved in the United States for use against anthrax, diphtheria, hepatitis A, hepatitis B, *Haemophilus influenzae* type b, human papillomavirus, influenza, Japanese encephalitis, Lyme disease, measles, meningococcal and pneumococcal diseases, mumps, pertussis, polio, rabies, rotavirus, rubella, shingles, smallpox, tetanus, tuberculosis, typhoid, varicella, and yellow fever. The vaccines being delivered can comprise live attenuated or killed bacteria, live attenuated viruses, subunit vaccines, conjugate vaccines, synthetic vaccines, viral vectors, polysaccharide vaccines, and DNA vaccines.

Further vaccines which may be delivered by means of the microprojection arrays of the invention may include vaccines (believed to be presently under development) directed against avian (pandemic) influenza virus, *Campylobacter* sp., *Chlamydia* sp., *Clostridium botulinum*, *Clostridium difficile*, dengue fever virus, *E. coli*, Ebola virus, Epstein Barr virus, nontypeable *Haemophilus influenzae*, Hepatitis C, Hepatitis E, Herpes viruses including Herpes zoster, HIV, leishmanial and malarial parasites, meningococcal serogroup B, parainfluenza, ragweed allergen, respiratory syncytial virus (RSV), Rift Valley fever virus, SARS-associated coronavirus, *Shigella* sp., *Staphylococcus aureus*, *Streptococcus* Group A (GAS), *Streptococcus* Group B (GBS), tick-borne encephalitis, Venezuelan equine encephalitis, and West Nile virus.

Among anthrax vaccines, particular preference is given to vaccines comprising the PA (protective antigen), particularly protective antigen which is recombinantly produced (rPA, meaning recombinant protective antigen). "Numerous studies have shown that PA is the most important antigen in natural and vaccine-induced immunity. PA is an 83-kDa protein which combines with lethal factor (LF) and edema factor (EF) to produce the *B. anthracis* binary toxins [lethal toxin and edema toxin] . . . . When presented to the immune system in an appropriate adjuvant, rPA derived from either *B. subtilis* or *B. anthracis* has also been shown to protect rodents and nonhuman primates from an aerosol challenge with fully virulent *B. anthracis* spores." E. D. Williamson et al., "Immunogenicity of Recombinant Protective Antigen and Efficacy against Aerosol Challenge with Anthrax," Infection & Immunity, vol. 73, pp. 5978 5987 (2005) (citations omitted).

Because of vaccines' widespread use, vaccine stability is an important consideration when there is a choice between multiple vaccines for a particular condition. When a vaccine is heat sensitive it is necessary to maintain a temperature-controlled supply chain for the vaccine, often referred to as a "cold chain." Cold chains for vaccines commonly target maintaining the vaccine at 2-8° C. This presents particular difficulties in poorer countries with hot climates. For certain vaccines, the solid-state environment of microprojection arrays of the invention may prove to be a more stable environment than maintaining them in solution.

It is desirable that the concentration of vaccine by weight in the microprojection arrays of the invention be comparatively high. This is believed to be desirable, for example, because it permits a higher concentration of antigen to be presented to the Langerhans cells when the microprojections are inserted in skin. Thus, for example, a concentration of at least about 0.1%, 0.5%, 1%, 2%, 5%, 10%, 15% or 20% by weight in the solids forming the array may be desirable.

The dose that is delivered to the body will be that appropriate to elicit a substantial immune response in a large majority of individuals, and may need to be determined empirically for particular vaccines. In general, a desirable dose may at least about 0.1 µg/cm$^2$, at least about 0.5 µg/cm$^2$, at least about 1 µg/cm$^2$, at least about 2 µg/cm$^2$, at least about 5 µg/cm$^2$, or at least about 10 µg/cm$^2$.

Alternatively, vaccine dose may be measured in units other than weight, for example activity units. Exemplary units for vaccine doses include CFU/mL—colony forming units (used, e.g., for the typhoid vaccine Vivotif® Berna, by Berna Products), ELISA units—enzyme-linked immunosorbent assay (used, e.g., for the hepatitis A vaccine Havrix® from GlaxoSmithKline), and TCID50—tissue culture infective dose (used, e.g., for the influenza vaccine FluMist, by MedImmune).

Alternatively, the vaccine dose may be measured as a percentage of the dose delivered by other paths, for example intramuscularly. It may be desirable, for example, to deliver at least about 1%, at least about 10%, at least about 25%, at least about 50%, at least about 75%, at least about 100%, at least about 150%, or at least about 200% of the dose delivered by other paths, for example of the dose delivered intramuscularly. Alternatively, it may be desired to deliver no more than about 200%, no more than about 150%, no more than about 100%, no more than about 75%, no more than about 50%, no more than about 25%, no more than about 10%, or no more than about 1% of the dose delivered by other paths.

As with conventional transdermal patches, dose delivery by a microprojection array may be less than the total vaccine content of the microprojection arrays.

B. Composition of the Microprojection Arrays

The microprojection arrays of the invention comprise a polymer. The polymer should be biocompatible. The polymer is preferably biodegradable. By the term "biodegradable" we mean that a composition will degrade under expected conditions of in vivo use (e.g., insertion into skin), irrespective of the mechanism of biodegradation. Exemplary mechanisms of biodegradation include disintegration, dispersion, dissolution, erosion, hydrolysis, and enzymatic degradation.

For example, suitable biocompatible, biodegradable polymers include poly(lactide)s (PLA), poly(glycolide)s (PGA), poly(lactide-co-glycolide)s (PLGA), polyanhydrides, polyorthoesters, polyetheresters, polycaprolactones (PCL), polyesteramides, poly(butyric acid), poly(valeric acid), polyvinylpyrrolidone (PVP), polyvinyl alcohol (PVA), polyethylene glycol (PEG), block copolymers of PEG-PLA, PEG-PLA-PEG, PLA-PEG-PLA, PEG-PLGA, PEG-PLGA-PEG, PLGA-PEG-PLGA, PEG-PCL, PEG-PCL-PEG, PCL-PEG-PCL, copolymers of ethylene glycol-propylene glycol-ethylene glycol (PEG-PPG-PEG, trade name of Pluronic® or Poloxamer®), dextran, hetastarch, tetrastarch, pentastarch, hydroxyethyl starches, cellulose, hydroxypropyl cellulose (HPC), sodium carboxymethyl cellulose (Na CMC), thermosensitive HPMC (hydroxypropyl methyl cellulose), polyphosphazene, hydroxyethyl cellulose (HEC), other polysaccharides, polyalcohols, gelatin, alginate, chitosan, dextran, hydroxyethyl starches, polyphosphazene, hyaluronic acid and its derivatives, collagen and its derivatives, polyurethanes and copolymers and blends of these polymers. Preferred solvents for casting include water, alcohols, (for example, C2 to C8 alcohols such as propanol and butanol), and alcohol esters, or mixtures of these. Other possible non-aqueous solvents include esters, ethers, ketones, nitriles, lactones, amides, hydrocarbons and their derivatives as well as mixtures thereof. Polymers which may be dissolved or dispersed in aqueous media are preferred.

In general the polymers used in the arrays of the invention may have a molecular weight of at least about 500 Daltons, at least about 1000 Daltons, at least about 5000 Daltons, at least about 10,000 Daltons, at least about 50,000 Daltons, or at least about 100,000 Daltons.

The biodegradability of a microprojection array may be facilitated also by the inclusion of sugars, which may also have a stabilizing effect on vaccine components. Exemplary sugars which may be included in a microprojection array include dextrose, fructose, galactose, maltose, maltulose, isomaltulose, mannose, lactose, lactulose, sucrose, and trehalose. Sugar alcohols, for example lactitol, maltitol, sorbitol, and mannitol, may also be employed. Cyclodextrins can also be used advantageously in microprojection arrays, for example α, β, and γ cyclodextrins, including hydroxypropyl-β-cyclodextrin and methyl-β-cyclodextrin.

The biodegradability of a microprojection array may be facilitated by inclusion of water-swellable polymers such as crosslinked PVP, sodium starch glycolate, crosslinked polyacrylic acid, crosscarmellose sodium, celluloses, natural and synthetic gums, polysaccharides, or alginates.

In a multilayer array as discussed below, the sugars and other polymers which facilitate biodegradability may be located only in a layer or layers which encompass the microprojections.

While the shape of the microprojections is not believed to be critical, in general it is preferred that they have a height of at least about 100 µm, at least about 150 µm, at least about 200 µm, at least about 250 µm, or at least about 300 µm. In general it is also preferred that the microprojections have a height of no more than about 1 mm, no more than about 500 µm, no more than about 300 µm, or in some cases no more than about 200 µm or 150 µm. The microprojections may have an aspect ratio of at least 3:1 (height to diameter at base), at least about 2:1, or at least about 1:1. A particularly preferred shape for the microprojections is a cone with a polygonal, for example hexagonal or rhombus-shaped, base. Other possible microprojection shapes are shown, for example, in U.S. Published Patent App. 2004/0087992.

It may be preferred that the microprojections have a sharp point or tip. A tip diameter of less than about 5 µm or 2 µm may be desirable. A tip diameter of less than about 1.5 µm is preferred, as is a tip diameter of less than about 1 µm.

The number of microprojections in the array may also be comparatively high, because each microprojection provides vaccine to a different site on the skin. The number of microprojections in the array is preferably at least about 100, at least about 500, at least about 1000, at least about 1400, at least about 1600, or at least about 2000. The area density of microprojections, given their small size, may not be particularly high, but for example the number of microprojections per cm$^2$ may be at least about 50, at least about 250, at least about 500, at least about 750, at least about 1000, or at least about 1500.

It is desirable that the microprojection array be at least somewhat flexible to accommodate the curvature of the human body. It is desirable, for example, that the array be sufficiently flexible that all or substantially all the microprojections be able to penetrate the skin of a typical patient when the array is applied with a suitable applicator to a convex body surface such as the upper arm.

C. Detachable Microprojections

In a further aspect of the invention, it may be desired that the microprojections of the array detach from the array following insertion of the array into skin. This may be accomplished by a number of approaches.

A layered approach, for example, may be used in which the array is composed of multiple layers, and a layer comprising the areas where the microprojections attach to the base of the array is more readily degradable than other layers.

One potential advantage of detaching microprojections is elimination of sharp disposal requirements. Another potential advantage of detaching microprojections is elimination of needle stick injury. Another potential advantage of detaching microprojections is elimination of misuse, for example needle sharing, since the substrate without microprojections or with microprojections whose tips have been blunted due to biodegradation will not penetrate the skin. Another potential advantage of detaching microprojections is the avoidance of drug misuse because drug enriched tips are dissolved in the skin and no or minimal drug is left in the array.

Alternatively, an array made of a homogeneous material may be employed, in which the material is more readily degradable at lower pH's. Arrays made of such a material will tend to degrade more readily near the attachment points because these, being closer to the surface of the skin, are at a lower pH than the distal ends of the microprojections. (The pH of the skin's surface is generally lower than that of the skin further inwards, pH being for example approximately 4.5 on the surface and approximately 6.5 to 7.5 inward.)

Materials whose solubility is dependent on pH can be, for example, insoluble in pure water but dissolve in acidic or basic pH environment. Using such materials or combination of materials, the arrays can be made to differentially biodegrade at the skin surface (pH approximately 4.5) or inside the skin. In the former, the whole array can biodegrade while in the latter, the microprojection portion of the array will biodegrade allowing the base substrate to be removed and discarded.

Materials whose degradability in an aqueous medium is dependent on pH may be made, for example, by utilizing the acrylate copolymers sold by Rohm Pharma under the brand name Eudragit, which are widely used in pharmaceutical formulation. A further example of a material with pH-dependent solubility is hydroxypropyl cellulose phthalate. Materials with pH-dependent solubility have been developed, for example, for use as enteric coatings in oral dosage forms. See, e.g., U.S. Pat. No. 5,900,252 and *Remington's Pharmaceutical Sciences* (18th ed. 1990).

D. Multilayer Arrays

It may be desirable for the microprojection array of the invention to comprise an additional layer in addition to the layer which comprises a polymeric material and the vaccine.

There are a number of reasons why arrays with multiple layers may be desirable. For example, it is often desirable that, compared to the whole volume of the microprojection array, the microprojections themselves have a higher concentration of active ingredient. This is so, for example, because the microprojections can be expected in many cases to dissolve more rapidly, being in a more hydrated environment than the base of the array. Furthermore, in some protocols for array application, the array may be left in for a short period of time during which essentially only the microprojections can dissolve to a substantial extent. The desirability of placing a higher concentration of active in the projections themselves is particularly acute when the active is costly. A way to achieve a higher concentration of active in the projections themselves is to have a first active-containing layer which includes the microprojections or a substantial proportion of the microprojections, and a second layer with a reduced or zero concentration of active which includes the base or a substantial proportion of the base.

E. Manufacturing the Microprojection Arrays

The microprojection arrays of the invention may be fabricated by the techniques for the fabrication of two-layer arrays which are disclosed in U.S. Provisional Patent Applications Nos. 60/923,861 and 60/925,262 (the priority documents for U.S. patent application Ser. No. 12/148,180). The application of these techniques in the context of vaccines is summarized here.

In general, an array of microprotrusions or microprojections is formed by (a) providing a mold with cavities corresponding to the negative of the microprotrusions, (b) casting atop the mold a solution comprising a biocompatible material, the vaccine, and a solvent, (c) removing the solvent, (d) demolding the resulting array from the mold.

The molds used to form the microprojections in methods of the invention can be made using a variety of methods and materials. The mold may, for example, conveniently comprise a ceramic material. Alternatively, for example, the mold may comprise a silicone rubber or a polyurethane. The mold may alternatively comprise a wax. A particular silicone rubber system which may be used is the Sylgard® system from Dow Corning (Midland, Mich.), for example Sylgard 184.

There are a number of ways of making the molds. The molds can be made, for example, by casting the liquid mold material over a master microprojection array and allowing the material to dry and harden. In some cases, curing of the material may take place during the drying process or if curing agents are added. Silicone rubbers and polyurethane are two types of materials that can be used to make molds in this way.

The molds can be made by heating the mold material until it melts. The liquid is then cast over the master microprojection array and the material is allowed to cool and harden. Waxes and thermoplastics are two classes of materials that can be used to make molds in this way.

The molds can be made by pressing the master microprojection array into the mold material. The mold material is preferably much softer than the microprojection array. The mold material can be heated to soften it. Waxes and thermoplastics are two types of materials that can be used to make molds in this way.

The molds can be made by plating metal (such as nickel, copper or gold) onto the master microprojection array.

The molds can be made by machining the cavities into the mold material. Electrostatic discharge machining (EDM) can be used to make cavities in metals. Reactive ion etching (RIE) can be used to create the cavities in silicon and other semiconductors.

The step of casting solution onto the molds may be performed by a number of methods known to those of skill in the art. Example 1 describes briefly a way of performing the step of casting. Goals of casting include roughly uniform coverage of the surface of the mold on which the microprojection array is expected to be formed.

The solution which is cast preferably comprises a polymer and the vaccine in a suitable solvent. Some preferred solvents for casting include water, alcohols, and alcohol esters.

In the step of casting the solution on the mold, it is commonly desired to avoid the presence of air bubbles between the solution and the mold when it is cast. A number of techniques may be employed within the methods of the invention for avoiding these bubbles.

An exemplary technique which may be employed to avoid air bubbles is to place the mold under compression prior to casting. The compression may be, for example, from two opposite sides. The compression will tend to reduce the volume of the cavities into which the solution must enter. The solution is then cast on the compressed mold. The compression is then released. Upon releasing the compression, the solution is drawn into the cavities as they expand to their normal volume. This process can be performed across the entire mold simultaneously or can be performed on sections of the mold.

If a bubble is not prevented from forming in a cavity, several methods can be used to remove the bubble. For example, the bubble may be dislodged by vibrating the mold with the drug solution on it.

Pressurization of the casting solution and mold helps to eliminate bubbles. In general, the gas in a bubble diffuses into the liquid over time. When this happens, drug solution flows into the cavity due to reduced pressure in the cavity and hydrostatic pressure. The filling and diffusion processes can be accelerated by pressurization. Drying of the liquid is preferably slowed during this period so the liquid can flow into the cavity as the gas from the bubble diffuses into the liquid. Pressurization can be accomplished by placing the mold with the drug solution on it into a pressure vessel. Pressurization may involve a pressure of at least about 3 psi, about 5 psi, about 10 psi, about 14.7 psi, or about 100 psi above atmospheric. Increasing the pressures increases the rate at which the residual gas diffuses into the liquid.

The Epstein-Plesset equation for the time to the dissolution of a bubble in a liquid gives at least a qualitative understanding of the bubble dissolution taking place when the mold and cast solution are pressurized. However, generally the bubbles in mold cavities will have roughly a conical shape and the bubbles hypothesized by Epstein and Plesset were spherical.

A vacuum can be applied after the drug solution is cast over the cavities to make the bubbles expand which increases the force pushing them up through the drug solution. The bubbles then rise to the surface of the liquid and the liquid fills the cavities. Drying of the liquid is preferably slowed during this period so the liquid can flow into the cavity as the bubble rises.

Thus, for example, an exemplary method of casting dispenses the solution on the mold over the cavities. A vacuum is applied, causing air trapped in cavities to expand. The air bubbles flow towards the surface of the solution, which in turn flows down into the cavities. When the pressure is returned to atmospheric, the expanded air left in the cavities compresses down.

Another method of casting begins by applying a vacuum to the mold, reducing the amount of air in the cavities, then dispenses the solution into the cavities, releases the vacuum and awaits for the formulation to be drawn into the cavities. The diffusion of the residual gas can again be sped up by applying pressure. At this point the residual solution can be removed from the substrate by scraping with a doctor blade across the top of the mold.

During the process of solvent removal, the volume of the cast solution will naturally diminish. With an appropriate choice of solvents, it is possible for the distal ends of the microprojections—those furthest from the base—to become finer as a result of solvent removal. Fineness in these tips may be favorable, all else being equal, for easier penetration of the skin, and may thus be desired.

The solvent removal may be accomplished, for example, by heat or vacuum. The solvent removal may be assisted by covering the cast solution with an absorbent material. However, because vaccines tend to be heat labile, it is desirable to avoid extensive use of heat in the solvent removal step because of the possibility of irreversible denaturation of the active. For example, it is preferable if no temperature above about 100° C. is used, more preferably no temperature above about 90° C., and more preferably no temperature above about 85° C. or 80° C. is employed. More preferably, no temperature above about 50° C., 40° C. or 37° C. or 35° C. is employed.

Where a second layer in the array is desired, the solution comprising the vaccine is cast so that it fills the cavities partially or fills no more than the cavities. This solution is dried. A further solution with a lower or zero concentration of active, constituting a second layer, is then cast over the solution comprising the active. The polymers and sugars used in the first layer are preferably not soluble in the solvent used for the second layer. The second layer preferably uses a different polymer or polymers from the ones used in the first layer.

The second layer may comprise, for example, cellulose acetate butyrate, cellulose acetate, cellulose acetate propionate, ethyl cellulose, nitrocellulose, hydroxypropyl methyl cellulose phthalate, polyacrylates (such as acrylate/octylacrylamide copolymers, Dermacryl 97), or polymethacrylates (such as Eudragits E, RL, RS, L100, S100, L100-55). Preferably where the first layer is cast in an aqueous solvent, the second layer is cast in an organic solvent. Preferred solvents for the second layer include alcohols, for example isopropyl alcohol and ethanol, and esters, for example ethyl acetate and propyl acetate.

F. Bioadheesive Polymers

In a further aspect of the invention, it may be desired that the microprojection array or a layer of the array comprise a polymer or polymer blend with certain bioadhesive characteristics, which within a certain range of moisture will have higher adhesive strength the greater the moisture. It is particularly preferred in a multilayer array that the layer or layers in which the microprojections principally lie possess bioadhesive characteristics.

While usable microneedles and microprojections may be made of a number of biodegradable polymers as indicated in the patents and patent applications cited in the background section, a polymer that has a bioadhesive character has the advantage that no additional array attachment mechanism, for example an additional adhesive arranged along the exterior perimeter of the microneedle array, may be needed. Use of a bioadhesive polymer may also facilitate detachment of the microneedles or microprojections because they will have a greater adhesion to the interior of the skin where there is greater moisture.

The bioadhesive polymers used in the methods of the invention may, for example, increase in adhesiveness from a moisture content of about 2%, about 5%, or about 10% to some upper limit of moisture content. The upper limit of moisture content beyond which adhesiveness ceases to increase is preferably at least about 20%, more preferably at least about 30%, 40%, 50%, 60% or 90% moisture content.

Exemplary polymers with bioadhesive characteristics include suitably plasticized polyacrylic acid, polyvinyl alcohol, and polyvinylpyrrolidone. An extensive discussion of a class of bioadhesive polymer blends is found in U.S. Pat. No. 6,576,712 and U.S. Published Patent Applications Nos. 2003/0170308 and 2005/0215727, which are incorporated by reference for their teaching of bioadhesive polymer blends and adhesion testing. Preferable bioadhesive polymers are those which possess hydrogen-bonded crosslinks between strands of the primary polymers. These crosslinks may comprise a comparatively small molecule which forms hydrogen bonds to two primary polymer strands. It is believed that certain sugars may act as a small molecule crosslinker in this manner with particular primary polymers such as polyvinyl alcohol.

The bioadhesive character of a polymer or blend may be determined by testing the bulk material for adhesion (e.g., by a peel test) at different levels of hydration. Alternatively, the bioadhesive character may also be seen if a microneedle array as applied to skin becomes more difficult to remove in minutes or tens of minutes after application, since the array may be assumed to become more hydrated during that period of time.

The bioadhesive nature of polymer may allow the polymer to form a channel or plug in the skin to keep pores open for prolonged period of time for drug diffusion. This is particularly useful if the substrate of the array is used as a drug reservoir, containing the same active ingredient or a different active ingredient from the one contained in the microneedles. The bioadhesive array can be also be used to pretreat the skin and leave bioadhesive microneedles inside the skin. This may be followed by application of a solid or liquid reservoir. Due to the channel formation, drug may freely diffuse through bioadhesive channels created and located in the skin.

G. Some Figures of Merit

A common FIGURE of merit for a vaccine administration system is the immunoglobulin G (IgG) titer achieved a particular time after exposure to the vaccine. Immunoglobulin M (IgM) becomes elevated quickly in earlier phases of the immune response, whereas IgG becomes elevated more slowly but in the longer term predominates together with immunoglobulin A (IgA). IgG is responsible for neutralization of viruses and bacterial toxins and facilitating destruction of bacteria by phagocytosis or lysis, and is thus a useful measure of the nature of the immune response raised against a particular antigen.

A further figure of merit for vaccine administration is the duration of the administration. It is generally preferred that the administration take no more than about 2 minutes, no more than about 5 minutes, no more than about 10 minutes, or no more than about 30 minutes. It is generally preferred, where the administration consists of inserting a microneedle array into skin, that the array is inserted in the skin for no more than about 2 minutes, no more than about 5 minutes, no more than about 10 minutes, or no more than about 30 minutes.

A further figure of merit for microprojection arrays is transepidermal water loss (TEWL) after application of the array, which is conveniently expressed in units of mass per unit area and time. TEWL measurement has a number of dermatological applications. Commercially available instruments exist for the measurement of TEWL, for example from Delfin Technologies Ltd., Kuopio, Finland. TEWL is conveniently measured before and after the application of a microneedle array to a human test subject, the ratio of the two measured values being an indication of the degree to which the microneedle array disrupts the barrier function of the skin.

For microneedle arrays it is desired that the ratio of TEWL's after and before application of the microneedles be at least about 1.2, at least about 1.5, more preferably at least about 2.0.

H. Applicators and Kits

The microprojection arrays of the invention may in some instances be applied manually simply by pressing them into skin. In practice, it may often be helpful for the microprojection arrays of the invention to be applied to the skin by means of some mechanism which helps insure a greater uniformity and/or reproducibility in the skin penetration. Such mechanisms may include, for example, the applicators disclosed in U.S. Provisional Patent Application No. 60/881,905, which is incorporated by reference. (U.S. Provisional Patent Application No. 60/881,905 is a priority document for U.S. Published Patent Application No. 20080183144.) Such mechanisms may be spring-loaded so that the array is driven into the skin using some of the energy stored in a spring.

The vaccine-containing arrays of the invention may be packaged in a kit together with, for example, a package insert, a desiccant, and/or an applicator. A number of vaccine-containing arrays may be packaged with an applicator, or alternatively there may be a single disposable applicator for each array which forms part of the kit for the array.

I. Discussion

The data of Example 4 below demonstrates the advantages of the microneedle arrays and methods of administration of the invention compared to intramuscular injection, which is presently the standard route of vaccine administration. Without wishing to be bound by theory, it is believed that a number of factors may have been responsible for the fact that epidermal delivery by inventive structures and formulations was more efficacious than intramuscular delivery:

1. The epidermis is a richer source of antigen presenting cells APCs compared to muscle. The higher the number of APCs that present the antigen, all else being equal, the higher the expected immune response.

2. Multiple skin barrier perforations (circa 1400 microstructures per array) may act to recruit APCs to the application site, or encourage them to proliferate.

3. The application of the microneedle arrays of the invention to skin, for example using a spring loaded applicator, may have produced a low grade inflammatory response which may have helped elicit a stronger immune response.

4. The high molecular weight of the polymeric component of the microneedle devices prevents rapid clearance of the molecule from the administration site. There is some evidence in the literature that PVA of similar molecular weight (133 kD) is irritating. C. E. Hall & O. Hall, "Polyvinyl alcohol: Relationship of physicochemical properties to hypertension and other pathophysiologic sequelae," *Laboratory Investigation*, vol. 12, p. 721 (1963). A low level of irritation caused by prolonged presence of the polymer may help to stimulate a stronger immune response.

5. The hypertonic nature of the formulations may enhance diffusion of the antigen into APCs or speed the rate of antigen uptake.

6. As they dissolve, the microneedle structures have a very high antigen concentration in comparison to that of the intramuscular formulation, by as much as tenfold. Higher antigen concentrations may drive diffusion into APCs.

7. Components of the formulations may serve to stabilize the rPA and thus preserve its immunogenicity. In an intramuscular formulation, rPA may degrade and become less immunogenic.

8. Components of the formulation may interact with the antigen and enhance its immunogenicity by creating more epitopes on the molecule.

9. Components of the formulations may cause aggregation of rPA molecules into higher molecular weight adducts, rendering them more immunogenic.

10. Microneedle devices access more APCs by virtue of the large area of skin treated—for example, 1400 separate administration sites per device. Thus, more APCs are presumably exposed to the antigen.

11. Antigen clearance from the epidermis via the lymph system, an integral part of the immune system, is slower than from muscle. Muscle is highly vascularized, and thus antigen is removed from the locale more quickly.

12. The rPA interacts with high molecular weight polyvinyl alcohol (PVA), probably by hydrogen bonding. Association with the PVA may slow down clearance of the antigen from the epidermis, maximizing the opportunity for interaction with APCs.

13. The viscous nature of the formulations as they dissolve in the skin essentially forms a depot of antigen, increasing its residence time in the tissue.

It is to be understood that while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

The following examples are put forth so as to provide those of ordinary skill in the art with a complete disclosure and description of how to implement the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric.

Example 1

General Process for Array Casting

The mold to be used to form a microneedle array is cleaned with water and dried in an incubator. The mold is then placed in a Petri dish. One dispenses a small amount of formulation, for example, 20 μL, on the mold. The formulation may contain, for example, 25% BSA (bovine serum albumin), 20% polyvinyl alcohol USP, 27% trehalose, and 28% maltitol in water solvent, such that the formulation has, for example, 20% solids content as applied. The formulation is spread manually over the mold using a transfer pipette with a trimmed tip. The formulation is then vortexed, for example for five seconds, using a commercial vibrating instrument to even out the formulation. The mold with the formulation covering it is placed in a pressure vessel under 1 atm for about 10 minutes. Pressure is then removed. The mold is placed in the incubator at a temperature of 32° C., for about 1 hr. The array may then be demolded, for example using double-sided adhesive tape, and optionally attached to a backing.

Example 2

General Process for Casting Two-Layer Arrays

Following the drying step of Example 1, an additional layer is cast on the mold using similar procedures. The additional layer may, for example, consist of 75 μL of 20 wt % Eudragit EPO in a 3:1 mixture of ethanol and isopropyl alcohol. The additional layer may be spread out, for example, using a glass slide. The mold is placed in a pressure vessel and pressurized at 1 atm for 2 minutes. The pressure is released and the mold is allowed to dry in the pressure vessel for an additional five minutes, without disturbing. The mold is again dried in the incubator for 1 hr at 32° C., and then demolded.

Example 3

Microneedle Arrays Comprising rPA

For an immunogenicity study in a rat model, microneedle structures containing an antigen (rPA, recombinant protective antigen from *Bacillus anthracis*) were fabricated from components that dissolve when they enter the skin, releasing antigen directly into the epidermis. The devices were produced by introduction of an aqueous casting solution to a micromold to make a microneedle array with 200 μm tall, 6-sided structures, at about 700 structures per cm$^2$, total area approximately 2 cm$^2$.

More specifically, the microneedle arrays were prepared with the following procedure. A 24/17 mm diameter PET (polyethylene terephthalate) ring, approximately 200 μm thick, with a PVP+PEG (polyvinylpyrrolidone+polyethylene glycol) adhesive layer, was attached to the microneedle mold base to form a boundary. Fifty μL of formulation was pipetted and spread. This was vortexed for 5 sec to homogenize the liquid layer and placed in a pressure cooker at 1 bar for 10 minutes. This was dried in the incubator at 32° C. for 1 hour. A 100 μL layer of Eudragit EPO (20% in 3:1 ethanol:isopropanol) was placed on top of the formulation layer and spread within the ring. This was placed in a pressure cooker at 1 bar for 2 minutes and then returned to atmospheric pressure for 10 minutes. This second layer was dried in the incubator at 32° C. for 1 hour. A 16 mm PET disc with adhesive was pressed on the back of the array, followed by a 24 mm PET disc with adhesive to provide additional support and aid removal of the array from the mold. These discs were also approximately 200 μm thick.

The film control was prepared with the following procedure: 10 μL of the antigen-containing formulation was dispensed on the non-release side of release liner and spread into a 1"×1" thin film. This was dried in the incubator for 30 minutes at 32° C. A 20 μl layer of Eudragit EPO (20% in 3:1 ethanol:isopropanol) was dispensed over the formulation layer. This was spread into an approximately 20 mm diameter circle within the boundaries of the formulation layer. The resulting composition was dried in the incubator for 30 minutes at 32° C. A PET layer with adhesive was pressed onto the back of the film.

Table 1 below indicates the composition of three microneedle casting formulations designated rPA Low, rPA Med, and rPA High, with the content of each ingredient given in % of solids. Table 1 also shows the composition of a non-microneedle film which was tested.

TABLE 1

|  | rPA | PVA | Trehalose | HP-β-CD | Maltitol |
|---|---|---|---|---|---|
| rPA Low | 2.5 | 20 | 31 | 15.5 | 31 |
| rPA Med | 5 | 20 | 30 | 15 | 30 |
| rPA High | 10 | 20 | 28 | 14 | 28 |
| Film | 10 | 20 | 28 | 14 | 28 |

None of the components of the microneedle arrays is a known adjuvant.

Example 4

Testing of rPA-Containing Microneedle Arrays

The microneedle arrays described in Example 3 were tested in vivo in anesthetized, female Sprague-Dawley rats, 5 per group. In preparation for the application of the treatments, an area of skin on the animals' side was shaved with clippers followed by an electric razor. Microneedle formulation arrays and films were each applied for two minutes. The skin sites were tested for transepidermal water loss (TEWL) before and after treatment. Microneedle arrays were inspected post use to measure the average % length of the needles that dissolved. Based on this value, an estimate of the amount of rPA delivered into the rat skin was made. The results are given in Table 2 below. Standard deviations are given in parentheses.

TABLE 2

|  | TEWL Ratio | % Dissolution | rPA Delivery (μg) |
|---|---|---|---|
| rPA Low | 3.8 (0.70) | 78.3 (8.1) | 5.1 (1.5) |
| rPA Med | 3.3 (0.32) | 77.2 (9.2) | 9.8 (2.9) |
| rPA High | 2.1 (0.38) | 75.8 (4.0) | 18.0 (2.9) |
| Film | 1.1 (0.22) | N/A | N/A |

All animals were primed intramuscularly with 10 μg rPA plus alum on day 0. A second boost immunization was carried out on day 28 using the formulations of Example 3, intramuscular injection (10 μg), intradermal injection with a syringe (10 μg and 1 μg), and no treatment. Serum was collected two weeks after each immunization on days 14 and 42.

FIG. 1 depicts the ratio of IgG titer of the first and second immunizations for each group of animals tested.

The IgG titer ratio was higher in sera from the animals treated with 10 μg rPA from dissolving devices than in those treated with 10 μg by intramuscular or intradermal injection.

The stronger immune response elicited by the microneedle arrays, when compared to the standard method of antigen administration (IM), could potentially offer higher levels of protective immunity and efficacy.

Table 3 below lists the values for ratios between the prime and boost IgG geometric mean titers depicted in FIG. 1.

TABLE 3

| Treatment Group | IgG Titer Ratio (2wp2/2wp1) |
|---|---|
| None | 2.99 |
| Film | 3.46 |
| ID 1 | 4.41 |
| ID 10 | 11.61 |
| IM 10 | 13.92 |
| rPA Low | 4.26 |
| rPA Med | 23.80 |
| rPA High | 39.35 |

We claim:

1. A microprotrusion array, comprising:
an approximately planar base and a plurality of microprotrusions, each microprotrusion having an attachment point to the base and a distal tip to penetrate skin, said plurality of microprotrusions comprised of a first layer and a second layer, said first layer comprising at least one polymer different from a polymer in the second layer,
the first layer comprised of (i) a biodegradable polymeric material, (ii) a component selected from a sugar, a sugar alcohol, a cyclodextrin, and a water-swellable polymer, and (iii) a vaccine against anthrax, said first layer disposed in at least the distal tip of each microprotrusion in the plurality of microprotrusions, and
wherein the biodegradable polymeric material has a molecular weight of at least about 10,000 Daltons.

2. The array of claim 1, wherein the vaccine lacks an adjuvant.

3. The array of claim 1, wherein at least some of the plurality of microprotrusions detach upon insertion into skin.

4. The array of claim 1, wherein the second layer is comprised of a biodegradable polymeric material selected from poly(lactic acid) (PLA), poly(glycolic acid) (PGA) and polyvinyl alcohol (PVA).

5. The array of claim 4, wherein the polyvinyl alcohol is 0-90% hydrolyzed.

6. The array of claim 1, wherein the sugar is selected from dextrose, fructose, galactose, maltose, maltulose, iso-maltulose, mannose, lactose, lactulose, sucrose and trehalose.

7. The array of claim 1, wherein the first layer further comprises a bioadhesive polymer and wherein the first layer adheres to human skin.

8. The array of claim 1, wherein the array is produced by a process comprising solvent casting.

9. The array of claim 1, wherein the concentration of the vaccine is at least 0.1% by weight of solids of a casting formulation from which the first layer is formed.

10. The array of claim 9, wherein the concentration of the vaccine is at least 5% by weight of solids of a casting formulation from which the first layer is formed.

11. The array of claim 1, wherein the microprotrusions are detachable from the planar base such that, once inserted into skin, the detached microprotrusions provide a depot of the vaccine.

12. The array of claim 1, wherein the first layer is homogeneous.

13. The array of claim 1, wherein the microprotrusions are no more than about 500 μm in height.

14. The array of claim 1, wherein the array is flexible.

15. The array of claim 1, wherein the component is a sugar or a sugar alcohol that is present in an amount such that a stability of the vaccine after one year of storage is comparable or greater than that of the same vaccine in aqueous solution in a closed vial.

16. The array of claim 1, wherein the vaccine and the polymeric material are cross-linked by hydrogen bonding.

17. A method of administering a vaccine against anthrax, comprising:
inserting into the skin of a patient an array according to claim 1.

18. The method of claim 17, wherein the vaccine lacks an adjuvant.

19. The method of claim 17, wherein the microprojections are left in the skin for no more than 30 minutes.

20. The method of claim 17, wherein the array is applied to the patient's skin by means of an applicator.

21. The method of claim 17, wherein the applicator is spring-loaded.

22. A method of preventing a disease caused by anthrax, comprising introducing into the skin at least about 50 discrete deposits comprising a vaccine against anthrax and a biodegradable polymer using the array according to claim 1.

23. The method of claim 22, wherein the discrete deposits are projections which form part of an array.

24. The method of claim 23, wherein the projections detach from the array.

25. The method of claim 22, wherein each discrete deposit comprises at least about 0.05 ng of vaccine.

26. The method of claim 22, where the initial concentration of vaccine in each discrete deposit is at least about 0.5% by weight.

27. The method of claim 22, wherein where the initial concentration of vaccine in each discrete deposit is at least about 5% by weight.

28. The method of claim 22, wherein the polymer and the vaccine are mixed together within each deposit.

29. The method of claim 22, wherein the discrete deposits are at a density no lower than about 50 deposits per $cm^2$ of skin surface.

30. A microprotrusion array, comprising:
an approximately planar base and a plurality of microprotrusions, wherein the microprotrusions are formed from a biodegradable polymeric material having a molecular weight of at least about 10,000 Daltons that comprises approximately 0.1-50% by weight of solids of a vaccine against anthrax to deliver at least about 2 $ng/cm^2$ of vaccine.

31. A kit comprising a microprotrusion array as in claim 1 and an applicator for inserting the microprotrusion array into human skin.

32. The array of claim 1, wherein the sugar alcohol is selected from sorbitol, lactitol, maltitol, and mannitol.

33. The array of claim 1, wherein the first layer is comprised of a biodegradable polymeric material selected from dextran and tetrastarch.

34. The array of claim 1, wherein the biodegradable polymeric material is dextran and the component is sorbitol.

* * * * *